United States Patent [19]

Dochniak

[11] Patent Number: 5,399,706

[45] Date of Patent: Mar. 21, 1995

[54] IMIDAZOLIDINONE DIAMINE AND DERIVATIVES THEREOF

[75] Inventor: Michael J. Dochniak, St. Paul

[73] Assignee: H. B. Fuller Licensing & Financing, Inc., Wilmington, Del.

[21] Appl. No.: 25,091

[22] Filed: Mar. 2, 1993

[51] Int. Cl.$^6$ .................. C07D 233/04; C07D 233/16; C07D 233/14; C07D 233/22; C07D 233/124

[52] U.S. Cl. ............................... 548/324.1; 548/324.5; 548/323.5; 558/367; 558/368; 558/452; 528/55

[58] Field of Search .......................... 548/324.1, 324.5; 528/55; 558/367, 368, 452; 564/490, 511

[56] References Cited

U.S. PATENT DOCUMENTS

| | | | |
|---|---|---|---|
| 2,531,013 | 11/1950 | Surrey | 564/490 X |
| 2,613,212 | 10/1952 | Hurwitz et al. | 548/324.1 X |
| 2,767,184 | 10/1956 | McKay et al. | 548/324.5 X |
| 2,840,546 | 6/1958 | Yost | 548/324.5 X |
| 2,840,561 | 6/1958 | Yost | 548/325.5 X |
| 2,858,319 | 10/1958 | De Benneville | 548/324.5 X |
| 3,169,991 | 2/1965 | Rogier | 564/490 X |
| 3,194,825 | 7/1965 | Brotherton et al. | 564/490 X |
| 3,222,402 | 12/1965 | Cooperman | 564/490 |
| 3,398,196 | 8/1965 | Miller et al. | 564/490 X |
| 3,428,646 | 2/1969 | Hellerbach | 548/324.1 X |
| 3,919,233 | 11/1975 | Rebling et al. | 548/324.1 X |
| 4,104,220 | 8/1978 | Sims | 548/324.1 X |
| 4,308,275 | 12/1981 | Durant et al. | 548/324.1 X |
| 4,314,067 | 2/1982 | Herman et al. | 548/324.1 X |
| 4,319,032 | 3/1982 | Sandri et al. | 548/324.1 X |
| 4,487,941 | 12/1984 | Sekmakas et al. | 548/324.5 |
| 4,632,957 | 12/1986 | Welsh et al. | 548/324.1 X |
| 4,845,297 | 7/1989 | Kumoi et al. | 564/490 X |
| 4,880,931 | 11/1989 | Abboud et al. | 548/324.1 X |
| 4,883,854 | 11/1989 | Coury et al. | 528/28 |
| 4,990,672 | 2/1991 | Johnson et al. | 564/490 |
| 5,138,016 | 8/1992 | Murdock et al. | 528/55 |
| 5,196,589 | 3/1993 | O'Lenick et al. | 564/493 |

FOREIGN PATENT DOCUMENTS

| | | | |
|---|---|---|---|
| 0622832 | 6/1961 | Canada | 548/324.5 |
| 04278 | 8/1966 | France | 548/324.5 |
| 2829198 | 1/1979 | Germany | 528/55 |
| 689705 | 4/1953 | United Kingdom | 548/324.1 |
| 0834411 | 5/1960 | United Kingdom | 548/324.1 |
| 0934979 | 8/1963 | United Kingdom | 548/324.1 |
| 91/12243 | 8/1991 | WIPO | 528/55 |

OTHER PUBLICATIONS

Tarbell et al, J. Amer. Chem. Soc., vol. 68, pp. 1217–1219(1946).

Whitmore et al, J. Amer. Chem. Soc., vol. 66, pp. 725–732 (1944).

Israel, et al, J. Med. Chem., 14, 1042–1047, (1971).

"Non-Voc Modifier to Improve the Gloss of Water-Borne Coatings", Fred Giles, Jr., Presented at Water-Borne & Higher-Solids Coatings Symposium, New Orleans, La., Feb. 6–8, 1991.

Chem. Abst., File CA record for DE 2150438 and File Registry record for 2-Imidazolidinone, 1-8 2-[(-2-aminoethyl)amino]-3-methyl-. (1972).

*Primary Examiner*—Floyd D. Higel
*Attorney, Agent, or Firm*—Vidas, Arrett & Steinkraus

[57] ABSTRACT

Imidazolidinone compounds of the formula:

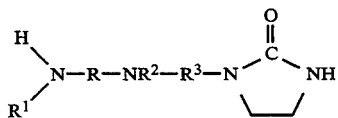

where R is a $C_3$–$C_5$ alkylene group, $R^1$ and $R^2$ are independently H or $C(=O)R^4$, $R^3$ is an aliphatic hydrocarbon group optionally substituted with one or more alkoxy groups or interrupted by one or more ether oxygen atoms, and $R^4$ is a hydrocarbon group substituted with an active hydrogen functional group are useful as chain extending monomers providing pendant imidazolidinone functionality to polyurethane/urea and epoxy polymers. The subject imidazolidinone compounds may also be incorporated into polyester/polyamide polyols or reacted to prepare radically polymerizable ethylenically unsaturated monomer and prepolymer compounds used in the synthesis of emulsion polymers.

4 Claims, 1 Drawing Sheet

IMIDAZOLIDINONE DIAMINE AND DERIVATIVES THEREOF

BACKGROUND OF THE INVENTION

Imidazolidinone functional groups have been reported to provide polymers with desirable properties in aminoplast resins and emulsion polymers. See, Gilles, Jr., et al, "Non-VOC Modifier To Improve The Gloss Of Water-Borne Coatings", presented at *Water-borne & Higher-solids Coating Symposium*, (Feb. 6–8, 1991), 268–278, U. So. Miss. Dept. of Poly. Sci.; U.S. Pat. No. 2,613,212; DE 2,829,198; and WO 91/12243. The various compounds disclosed in these references for incorporating imidazolidinone functionality into polymers all have structural features which limit the ability to incorporate the desired functional group into certain types of polymeric materials. In particular, the prior art structures offer very limited possibilities for incorporating pendant, non-terminal imidazolidinone functional groups into polymeric structures. There therefore exists a need for further compounds which can act as monomers for introducing imidazolidinone functionality in polymers of various types, particularly in the form of pendant non-terminal imidazolidinone groups.

In U.S. Pat. No. 3,919,233 certain imidazolidinone diamine compounds are reported as intermediates for the synthesis of antiviral compounds. Such imidazolidinone diamine compounds, however, do not have a ureido hydrogen atom on the imidazolidionone ring.

SUMMARY OF THE INVENTION

The invention, in a first aspect, comprises an imidazolidinone compound of the formula:

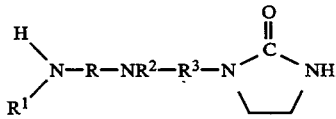

where R is a $C_3$–$C_5$ alkylene group, $R^1$ and $R^2$ are independently H or $C(=O)R^4$, $R^3$ is an aliphatic hydrocarbon group optionally substituted with one or more alkoxy groups or interrupted by one or more ether oxygen atoms, and $R^4$ is a hydrocarbon group substituted with an active hydrogen functional group.

The compounds of the previous formula are useful as chain extending monomers providing pendant imidazolidinone functionality to polyurethane/urea and epoxy polymers, and such polymers comprise further aspects of the invention.

The imidazolidinone compounds of the invention may also be incorporated into polyester/polyamide polyols or further reacted to prepare radically polymerizable ethylenically unsaturated monomer and prepolymer compounds which comprise still further aspects of the invention.

The pendant ureido hydrogen functionality present in the imidazolidinone group may be utilized as a crosslinking site for polymers of the invention, e.g., with melamines, and crosslinking formulations employing of the invention and a melamine comprise still further aspects of the invention.

A still further aspect of the invention are novel nitrile compounds utilized in the preparation of the imidazolidinone compounds of the invention.

These and still further aspects of the invention may be better appreciated with reference to the following detailed description of the invention.

DETAILED DESCRIPTION OF THE INVENTION

Figure 1:
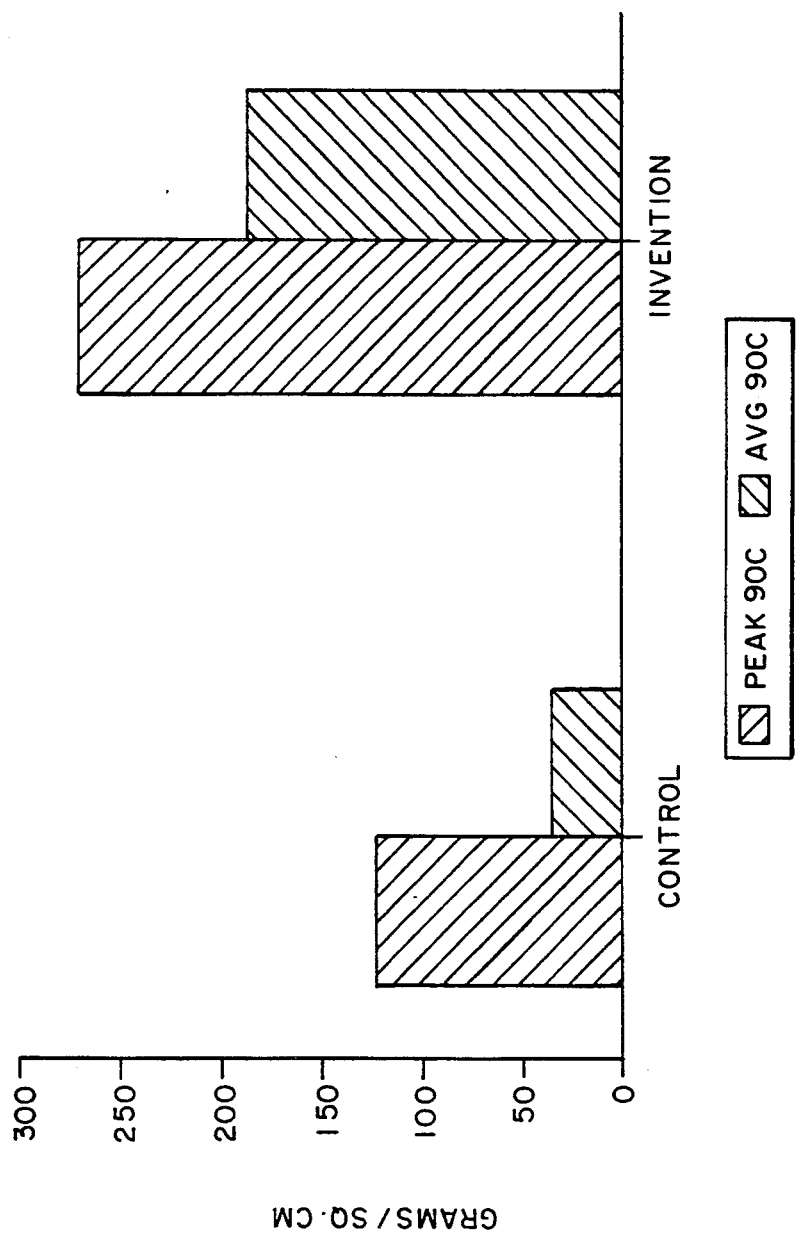
FIG. 1 is a graph showing comparative elevated temperature adhesion performance on a vinyl/ABS substrate using waterborne adhesives prepared from a polymer of the invention and from a control polymer, as described in Example 8.

The imidazolidinone compounds of the invention contain two nucleophilic sites which may react with polyester polyols, isocyanate or epoxy groups. As used herein, amido and ureido hydrogen atoms are not active hydrogen atoms. When $R^1$ and $R^2$ are H, the respective primary and secondary amino groups, of which the $R^1$ and $R^2$ hydrogen atoms are a part, provide these sites. When either $R^1$ or $R^2$ is $C(=O)R^4$, the active hydrogen group on $R^4$ provides an active hydrogen site. An example of an active hydrogen functional group with which $R^4$ may be substituted is hydroxyl. The two sites of active hydrogen atoms allow the compounds to be used as chain extenders for polyurethane and epoxy polymers.

The compounds of the invention are further characterized by the presence of a ureido hydrogen atom on the imidazolidinone ring. The ureido hydrogen atom on the imidazolidinone group contributes to improved adhesion properties obtained with polymers of the invention and also provides a site for melamine crosslinking to improve heat and solvent resistance properties of polymers formed from the compounds of the invention.

Preparation of the compounds of the invention involves the steps of cyanoalkylation of an amine of the formula:

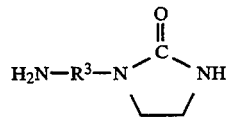

using a suitable cyanoalkylating reagent such as acrylonitrile, 2-butenenitrile or 2-pentenenitrile, followed by reduction of the cyano group on the resulting adduct to produce an imidazolidinone diamine of the invention having the formula:

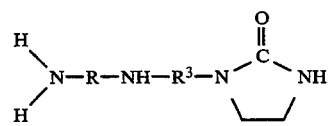

where R for the specific examples mentioned is —$CH_2CH_2CH_2$—, —$CH_2CH_2CH(CH_3)$— or —$CH_2CH_2CH(C_2H_5)$—, respectively. These diamines may be utilized to produce further compounds of the invention by reaction of the amine with an agent forming an organic group having an active hydrogen group thereon. For instance, reaction of the diamine with ethylene carbonate produces derivative compounds of the formulae:

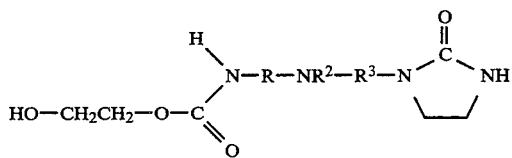

and/or

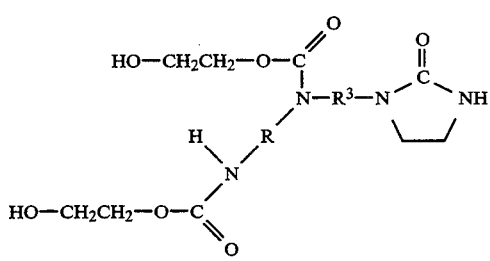

Like the starting diamine, these derivative compounds retain two sites of active hydrogen groups, thereby providing utility as chain extending monomers for polyurethane/urea or epoxy polymers.

Cyanoalkylation procedures are well known in the art. A representative literature example is Bruson "*Cyanoethylation*", *Organic Reactions*, Volume V, edited by R. Adams, John Wiley and Sons, Inc., New York, 1949. Commercial cyanoalkylation service is offered by Exxon Chemical Co. and by E. I. DuPont de Nemours Inc. The products of the cyanoalkylation reaction are novel nitrile adduct compounds of the formula:

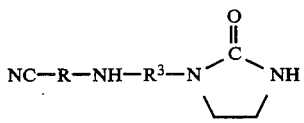

where R and $R^3$ are as previously defined. Reduction of these nitrile compounds, using reagents such as alkali borohydrides, $H_2$/Raney nickel, etc., also follows procedures well known in the literature and can be obtained as a contract service by the same companies. An example of a literature reduction is found in Winas, U.S. Pat. No. 2,334,140 (1943); *Chem. Abst.*, 38, 2666 (1944).

The compounds of the invention provide numerous advantageous properties to polymers into which they become incorporated. Pendant imidazolidinone functionality enhances polarity, improving adhesion of many polymer products of the invention. By providing the imidazolidinone group on a chain extending monomer, polymer molecular weight can be built up while assuring extensive distribution of the imidazolidinone group throughout the polymer network. In reactions with isocyanates, the diamine compounds of the invention provide urea linkages having improved chemical resistance over carbamate linkages, as well as better internal polymer strength and heat resistance due to hydrogen bonding.

Preferred compounds of the invention (i.e., where R is —$CH_2CH_2CH_2$—, and $R^1$, and $R^2$ equal H) are water soluble, allowing chain extension of isocyanate terminated prepolymers in aqueous phase to increase the molecular weights of water dispersible polyurethanes.

Chain extended polymers produced from the compounds of the invention are characterized by the presence of a plurality of groups of the formula:

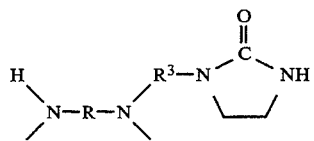

where R and $R^3$ are as previously defined.

The compounds of the inventions may also be further reacted to prepare radically polymerizable ethylenically unsaturated monomer and prepolymer compounds having pendant imidazolidinone functionality. Such compounds may be prepared by reaction of an ethylenically unsaturated compound having an isocyanate or epoxy functional group with a compound of the invention having the formula:

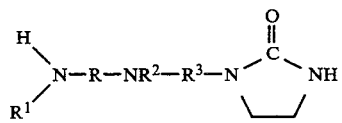

where R is a $C_3$–$C_5$ alkylene group and $R^1$ and $R^2$ are independently H or $C(\!=\!O)R^4$, $R^3$ is an aliphatic hydrocarbon group optionally substituted with one or more alkoxy groups or interrupted by one or more ether oxygen atoms, and $R^4$ is a hydrocarbon group substituted with an active hydrogen functional group. Suitable examples of ethylenically unsaturated epoxy or isocyanate compounds include, for instance, isocyanatoethyl methacrylate, vinyl glycidyl ether and a mono-, di-, or tri-isocyanate of the formula:

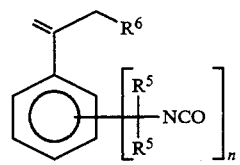

where each $R^5$ is independently a $C_{1-6}$ alkyl, $R^6$ is H or $R^5$ and n is 1–3.

An alternative method of preparing ethylenically unsaturated imidazolidinone compounds within the scope of the invention is to react a plural isocyanate or epoxy functional compound with both an ethylenically unsaturated compound having an active hydrogen functional group, and an imidazolidinone compound of the invention having the formula:

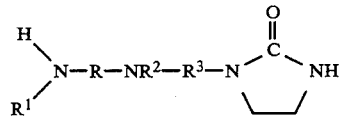

where R is a $C_3$–$C_5$ alkylene group, $R^1$ and $R^2$ are independently H or $C(\!=\!O)R^4$, $R^3$ is an aliphatic hydrocarbon group optionally substituted with one or more alkoxy groups or interrupted by one or more ether oxygen atoms, and $R^4$ is a hydrocarbon group substituted with an active hydrogen functional group. Suitable examples of ethylenically unsaturated compounds having active hydrogen groups include allylalcohol, allylamine, acrylic acid, hydroxyethyl acrylate, hydroxypropyl acrylate, diethylene glycol monoacrylate, triethylene glycol monoacrylate, polyethylene glycol monoacrylate, hydroxyethyl methacrylate, hydroxypropyl methacrylate, diethylene glycol monomethacrylate, triethylene glycol monomethacrylate, polyethylene glycol monomethacrylate, crotonic acid, itaconic acid, maleic acid, fumaric acid and half esters of maleic and fumaric acids.

The invention is illustrated by the following non-limiting examples.

MONOMER PREPARATION EXAMPLES

Example 1

Cyanoethylation of 1-(2-aminoethyl)imidazolidinone (AEI) with acrylonitrile in isopropanol solvent (20% by wt.) was accomplished using the commercial cyanoethylation process of Exxon Chemical Co. Reduction of the resulting reaction mixture was accomplished using H₂/Raney nickel in an autoclave.

The reaction product of the reduction step was purified by wipe film evaporation in three stages. The unit used was a glass Distact ™ still designed for lab scale. The still had a surface area of 0.06 m² and was equipped with a graduated feed, precision pumps to feed the evaporator, a vane vacuum pump, and a diffusion pump for very low vacuums (micron range). The condenser was cooled with an alcohol solution and the cold trap was cooled with liquid nitrogen.

The first stage used relatively poor vacuum levels, 90 mm Hg, and low temperatures (83°–85° C. evaporator, 0° C. condenser) to remove the isopropanol process solvent and any residual n-propyl amine (reduction product of unreacted acrylonitrile). The yield of undistilled residue from this step was 79.6%.

In the second stage the evaporator was kept at 130° C. and the condenser was at 70° C. The vacuum level was maintained at 0.007 mm Hg or 7 microns. Approximately 17% of the residue of the first stage was removed as distillate and identified as AEI and diamine product.

The final stage (evaporator 162°–165° C., condenser 70° C., vacuum 0.006 mm Hg) removed the diamine product from the bottoms. The split was 79.8% distillate to 20.2% residue. The distillate was a water-white, odorless, semi-viscous liquid completely soluble in water and providing a pH in 1% aqueous solution of 11.5. Carbon 13 NMR analysis revealed the product to contain about 18% of the starting monoamine, AEI, and 82% of the desired diamine:

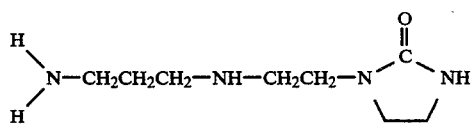

Overall yield from the purification was 53%.

Example 2

Cyanobutylation of AEI with 2-pentenenitrile is accomplished in water dispersion using the commercial cyanobutylation process of E. I. DuPont de Nemours Inc. Reduction and purification is accomplished as in the previous example to produce a product which is predominantly the diamine:

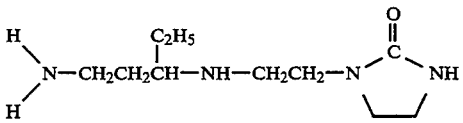

Example 3

The product of Example 1 is reacted with ethylene carbonate (mole ratio 1:2) at 80° C. to produce a compound of the formula:

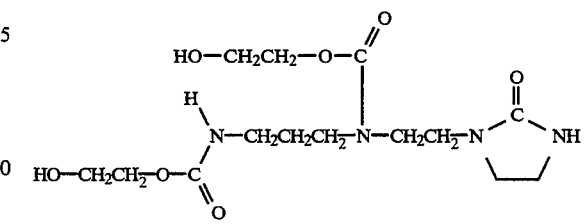

Example 4

Hydroxyethylethyleneurea is cyanoethylated with acrylonitrile and reduced in the manner of Example 1 to produce a monoamine of the formula:

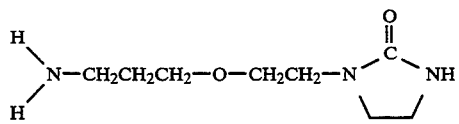

This monoamine is then cyanoethylated and reduced as in Example 1 to provide a diamine of the invention having the formula:

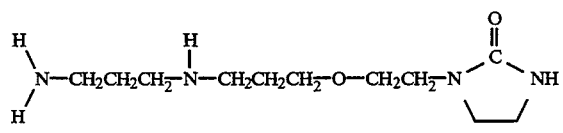

POLYMER PREPARATION EXAMPLES

Example 5—Non-ionic Polyurethane/urea Dispersion

To a reaction flask was charged 65.3 gm (0.1306 Eq) polyethylene glycol, 25.81 gm (0.2325 Eq) isophorone diisocyanate and two drops of Metacure ™ T-12 dibutyl tin dilaurate. This mixture was heated for 3 hours at 90° C. using overhead stirring. When the isocyanate content reached approximately 4.7% one hundred grams of deionized water was charged to disperse prepolymer. To 50 gm deionized water was charged 9.1 gm of the imidazolidinone diamine product of Example 1 and this mixture was added to reaction vessel over a 3 minute period. Properties of the dispersion and test results are as follows:

pH=8.9
Viscosity=3,850 mPas
Solids=39.27%

To this dispersion was added 5% by weight Desmodur DA (water dispersible polyfunctional isocyanate). The formulation was then applied to particle board by spraying and dried for 10 minutes. Substrates were vacuum formed using heat and aged 24 hours at ambient room temperature. 180 degree peel results:
- peak reading = 1409 g/cm
- valley reading = 204 g/cm
- average peel value = 1154 g/cm The peak and average values are determined by using a slip/peel tester (Model SP-101B, IMASS Inc). The slip/peel tester measures the coefficient of friction between surfaces or peel strengths of adhesives. The test speeds were set at 2 inches (5.08 cm) per minute for 60 seconds.

Example 6—Anionic Polyurethane/urea Dispersion

To a reaction flask with efficient stirring and heating was charged 423 gm (0.3021 eq) butane diol adipate polyester polyol, 3.0 gm (0.0671 eq) trimethylolpropane, 19 gm (0.2836 eq) dimethylolpropionic acid, 141 gm (0.1156 eq) meta-tetramethylxylene diisocyanate, and 13.6 gm (0.1344 Moles) triethylamine. The mixture was heated approximately 3 hours at 90° C. When the prepolymer reached 3.5% isocyanate 903.25 gm deionized water was added to disperse. To 50 gm deionized water was charged 27.92 gm of the imidazolidinone diamine product of Example 1, 5.22 gm monoethanolamine and 2.76 gm diethylenetriamine. This mixture of mono, di, and tri-functional amines were added to the dispersion over a 3 minute period. Physical properties of dispersion and test results are as follows:

pH = 7.87
Viscosity = 3,150 mpas
Solids = 40.24%
Particle size: Effective diameter = 74 nanometers
Mean diameter = 63 nanometers A 2 ml dry film was applied to PVC substrates which were then joined under 50 psi pressure at the temperatures given below for 30 seconds. The loads at which the bond failed when tested under T-peel conditions are given below.
- 125° F. = 284 g/cm
- 150° F. = 618 g/cm
- 175° F. = 1151 g/cm
- 200° F. = 1199 g/cm

Example 7—Emulsion Polymerized Imidazolidinone Functional Latex

In a 100 ml round bottom flask was charged 95.10 gm acetone, 50.14 gm Jeffamine® ED-2001 polyethoxylated/propoxylated diamine, 6 gm of the imidazolidinone diamine of Example 1 and 3 gm allylamine. The mixture was heated and stirred until the ingredients were disolved and then 19.8 gm tetramethylxylenediisocyanate was added slowly. The mixture was then refluxed until isocyanate, as monitored by infrared, had substantially all been consumed. The acetone solvent was then removed by evaporation, yielding an allylic imidazolidinone functional oligomer.

To a two liter flask equipped with stirrer, condenser, nitrogen inlet, temperature controlled water bath and monomer addition pump were charged 236.1 gm of deionizes water. The water bath was heated so as to provide a reaction temperature of 65° C. Five percent of a monomer mixture containing 134.5 gm deionized water, 36.8 gm of 30 mole ethoxylated octylphenol surfactant, 221 gm butyl acrylate, 157.6 gm methyl methacrylate, 5.9 gm methacrylic acid and 42.7 gm of the allylic imidazolidinone functional oligomer of the previous paragraph was charged to the reaction vessel. 1.24 gm each of ammonium persulfate and sodium metabisulfite were then added to the vessel to initiate the polymerization reaction. The remainder of the monomer mixture was added over a three hour period. Meanwhile, additional feeds of 1.29 gm ammonium persulfate in 24 gm deionized water and 1.29 gm sodium metabisulfite in 24 gm deionized water were added to the reactor vessel over a time period of 4 hours. One half hour after the addition of the catalyst was complete, the contents of the reactor were cooled and discharged.

The product was an aqueous latex having a solids content of 46.0%, a pH of 6.0, a particle size of 210 nm, a Brookfield viscosity of 40 mPas, and coagulum content of only 0.1%. The polymer had an intrinsic viscosity of 0.335 and an acetone insoluble content of 61%.

Example 8

To a reaction flask fitted with overhead stirrer, thermometer and nitrogen inlet is charged a polyester polyol along with 5% by weight of the imidazolidinone diamine of example 1. The mixture is heated to 85°–90° C. and amine number monitored to determine reaction completion. The product is a polyester/polyamide polyol.

COMPARATIVE PERFORMANCE EXAMPLE

Example 9

The imidazolidinone diamine product of Example 1 was incorporated into a thermoforming water dispersible polyurethane and compared with a control formulation utilizing the same number of equivalents of mono, di, and triamine. The formulations are shown in Table 1.

TABLE 1

| Component Number | Component | Equivalents of active group Control | Equivalents of active group Invention |
|---|---|---|---|
| 1 | Hexanedioic acid/butanediol polyester diol (Rucoflex ™ S-102-40) | 0.3021 | 0.3021 |
| 2 | Trimethylolpropane | 0.0671 | 0.0671 |
| 3 | Dimethylolpropionic acid | 0.2836 | 0.2836 |
| 4 | 1,3-Bis(1-isocyanato-1-methylethyl)-benzene | 1.156 | 1.156 |
| 5 | Monoethanolamine | 0.1245 | 0.0856 |
| 6 | Ethylenediamine | 0.2463 | — |
| 7 | Example 1 product: Equivalents diamine Equivalents monoamine | — — | 0.2463 0.0389 |
| 8 | Diethylene triamine | 0.0811 | 0.0811 |

The respective formulations were prepared by drying component (1) under vacuum in a clean reactor at 110° C. for 1 hour; adding components (2), (3) and (4) with agitation and holding the temperature at 90° C. for 4 hours (NCO content approximately 3.5%); adding the amines (5)–(8) to a sufficient quantity of deionized water to provide a 39.25% solids formulation when added to the reactor; and then adding the amine/water mixture to the reactor over a 3 minute period. Properties of the respective dispersions were as follows:

| Control | Invention |
|---|---|
| pH = 8.0 | pH = 8.0 |
| Viscosity = 50 mPas | Viscosity = 260 mPas |
| Solids = 39.2% | Solids = 39.3% |

| Control | Invention |
|---|---|
| Mean particle size = 89 nm | Mean particle size = 63 nm |

Heat activating temperatures of the two polymer dispersions were tested on untreated vinyl and results indicated substantially similar heat activating properties. The two dispersions were then tested on ABS/vinyl with 5% Desmodur DA as a polyfunctional isocyanate crosslinker and a heat activation temperature of 50° C. for 20 seconds was applied. After a 24-hour period at room temperature, peel values on both polymers gave vinyl failure. The two dispersions were also tested at 90° C. for 24 hours and results, shown graphically in FIG. 1, demonstrate that the dispersion employing the invention polymer with imidazolidinone functionality dramatically improved adhesion at these elevated temperatures.

What is claimed is:

1. A compound of the formula:

$$\underset{R^1}{\overset{H}{\diagdown}}N-R-NR^2-R^3-N\underset{\diagdown\_\_/}{\overset{\diagup\overset{O}{\overset{\|}{C}}\diagdown}{}}NH$$

where R is either a $C_4$–$C_5$ alkylene group and $R^1$ and $R^2$ are independently H or $C(=O)OR^4$, or R is a $C_3$ alkylene group and one of $R^1$ and $R^2$ is $C(=O)OR^4$ and the other is H or $C(=O)OR^4$, $R^3$ is an alkylene group which is unsubstituted or substituted with one or more alkoxy groups or interrupted by one or more ether oxygen atoms, and $R^4$ is a alkyl group substituted with a hydroxyl group.

2. A compound as in claim 1 wherein $R^3$ is ethylene or propyleneoxyethylene.

3. A compound selected from the group consisting of:

$$\underset{HO-CH_2CH_2-O-C\diagdown_O}{\overset{H}{\diagdown}}N-R-NR^2-R^3-N\underset{\diagdown\_\_/}{\overset{\diagup\overset{O}{\overset{\|}{C}}\diagdown}{}}NH,$$

$$\underset{\underset{HO-CH_2CH_2-O-C\diagdown_O}{\overset{H}{\diagdown}N\diagdown_R}}{\overset{HO-CH_2CH_2-O-C\diagup^O}{\diagdown}}N-R^3-N\underset{\diagdown\_\_/}{\overset{\overset{O}{\overset{\|}{C}}\diagdown}{}}NH$$

and mixtures thereof wherein R is a $C_3$–$C_5$ alkylene group $R^3$ is an alkylene or alkyleneoxy alkylene group.

4. A compound of the formula:

$$\underset{R^1}{\overset{H}{\diagdown}}N-R-NR^2-R^3-N\underset{\diagdown\_\_/}{\overset{\diagup\overset{O}{\overset{\|}{C}}\diagdown}{}}NH$$

wherein R is a $C_4$–$C_5$ alkylene group, $R^1$ and $R^2$ are H and $R^3$ is alkylene or alkyleneoxyalkylene.

* * * * *